(12) United States Patent
Hamer et al.

(10) Patent No.: US 6,413,548 B1
(45) Date of Patent: Jul. 2, 2002

(54) PARTICULATE ENCAPSULATION OF LIQUID BEADS

(75) Inventors: Monica A. Hamer, Woodbury; James J. Marti, St. Paul; William A. Hendrickson, Stillwater, all of MN (US)

(73) Assignee: Aveka, Inc., Woodbury, MN (US)

( * ) Notice: Subject to any disclaimer, the term of this patent is extended or adjusted under 35 U.S.C. 154(b) by 0 days.

(21) Appl. No.: 09/568,272

(22) Filed: May 10, 2000

(51) Int. Cl.⁷ .............................. A61K 9/14; B32B 15/02
(52) U.S. Cl. ............... 424/489; 428/402.2; 428/402.21; 428/403; 428/407; 424/490; 424/491; 424/493; 424/497; 424/498
(58) Field of Search .................. 428/402.2, 402.21, 428/403, 407; 424/489, 490, 491, 493, 497, 498

(56) References Cited

U.S. PATENT DOCUMENTS

| | | | |
|---|---|---|---|
| 4,680,173 A | 7/1987 | Burger | 424/47 |
| 5,500,223 A | 3/1996 | Behan et al. | 424/451 |
| 5,876,755 A | 3/1999 | Perring et al. | 424/489 |
| 6,126,926 A | 10/2000 | Tanaka et al. | |

FOREIGN PATENT DOCUMENTS

| | | |
|---|---|---|
| EP | 0 478 326 A1 | 4/1992 |
| EP | 0 539 142 A1 | 4/1993 |

OTHER PUBLICATIONS

Abstract for Japanese Patent No. 5065212A2; Issued Mar. 19, 1993.
Abstract for Japanese Patent No. 264813A2; Issued Sep. 26, 2000.
Abstract for Japanese Patent No. 11130614A2; Issued May 18, 1999.
Abstract for Japanese Patent No. 10265367A2; Issued Oct. 6, 1998.
Abstract for Japanese Patent No. 6211620A2; Issued Aug. 2, 1994.
Abstract for Japanese Patent No. 6166611A2; Issued Jun. 14, 1994.
Abstract for Japanese Patent No. 5085212; Issued Mar. 19, 1993.
Abstract for Japanese Patent No. 08211620; Issued Aug. 2, 1994.
Abstract for Japanese Patent No. 06066611; Issued Jun. 14, 1994.

Primary Examiner—Samuel A. Acquah
(74) Attorney, Agent, or Firm—Mark A. Litman & Assoc. P.A.

(57) ABSTRACT

Various materials, including generally non-compatible materials may be provided from a single delivery system by a unique encapsulation system. An encapsulation system is advantageously constructed as a core of aqueous liquid having at least 5% by weight water therein, and an encapsulant surrounding the core to form a stable encapsulated particle, the encapsulant comprising at least one layer of hydrophobic particles in contact with and surrounding the core, the core and hydrophobic particles providing an encapsulated system that has an average weight average particle diameter of from 0.05 to 25 micrometers and can support its own weight. The encapsulation system may be provided by a novel method of manufacture comprising providing a mass of hydrophobic particles having average mass diameter size of between 0.05 and 25 micrometers, providing droplets of an aqueous medium to the mass of particles, gently mixing the fine particles of aqueous medium and the hydrophobic particles to form a stable encapsulant system of droplets of the aqueous medium encapsulated by a shell of particles.

25 Claims, 2 Drawing Sheets

PARTICULATE ENCAPSULATION OF LIQUID BEADS

BACKGROUND OF THE ART

1. Field of the Invention

The present invention relates to the carrying of liquid materials within a readily rupturable form that can be easily released. In particular, the liquid materials may be provided in the form of a relatively stable encapsulation or microencapsulation that can be applied to a surface leaving little observable residue of the encapsulation mechanism.

2. Background of the Invention

The use of membranes, coatings, and capsules for the controlled release of liquid materials is well known in the art of both agricultural and non-agricultural chemicals. In agriculture, controlled-release techniques have improved the efficiency of herbicides, insecticides, fungicides, bactericides, and fertilizers. Non-agricultural uses include encapsulated dyes, inks, pharmaceuticals, flavoring agents, and fragrances. The most common forms of controlled-release materials are coated droplets or microcapsules, coated solids including both porous and non-porous particles, and coated aggregates of solid particles. In some instances, a water-soluble encapsulating film is desired, which releases the encapsulated material when the capsule is placed in contact with water. Other coatings are designed to release the entrapped material when the coating is ruptured by external force. Still further coatings are porous in nature and release the entrapped material to the surrounding medium at a slow rate by diffusion through the pores. In addition to providing controlled release, such coatings also serve to facilitate the dispersion of water-immiscible liquids into water and water-containing media such as wet soil. Droplets encapsulated in this manner are particularly useful in agriculture, where water from irrigation, rain, and water sprays is frequently present. A variety of processes for producing such capsules is known.

In one well-known process, capsules are formed by phase separation from an aqueous solution through the coacervation of a hydrophilic colloid sol. This is described in U.S. Pat. Nos. 2,800,457 (Green et al., Jul. 23, 1957) and 2,800,458 (Green, Jul. 23, 1957). An interfacial polymerization process is disclosed in U.S. Pat. Nos. 4,046,741 (Scher, Sep. 6, 1977) and 4,140,516 (Scher, Feb. 20, 1979), where film-forming reactants are dissolved in a hydrophobic liquid that is dispersed in water, the shell-forming reaction occurring at the interface when the phases are placed in contact as an emulsion. Another interfacial polymerization process is described in U.S. Pat. No. 3,726,804 (Matsukawa et al., Apr. 10, 1973) where all the film-forming ingredients initially reside in hydrophobic droplets also contain a low boiling or polar solvent in addition to the material to be encapsulated. Upon heating, the solvent is released into the aqueous phase (the continuous phase of the emulsion), and the film-forming materials accumulate at the interface and polymerize.

Olefin polymerization using a peroxide catalyst is described in Japanese patent publication No. 9168/1961, where an oil-insoluble polymer is formed at the surfaces of oil drops.

British Pat. Nos. 952,807 and 965,074 describe a process where a solid such as wax or a thermoplastic resin is melted, dispersed and cooled to form an encapsulating film around liquid droplets.

Microencapsulation of fragrances and hydrophobic liquid fill via the polyoxymethyleneurea (or urea-formaldehyde) method is taught by (Matson, 1970) U.S. Pat. No. 3,516,846.

U.S. Pat. No. 3,111,407 (Lindquist et al., Nov. 19, 1963) describes a spray drying method that forms encapsulated droplets at the instant of atomization.

U.S. Pat. No. 5,342,597 describes a method of providing "dry water" by mixing water and fumed silica under strong mixing conditions, providing a water droplet covered by silica particles in a highly distributional form, with low concentrations, if any, of true spheres of water surrounded by spherically disposed silica particles.

U.S. Pat. No. 4,008,170 discloses another format for providing silica and water, but not in an encapsulated silica shell water core format.

U.S. Pat. No. 6,045,650 describes surfaces that have coatings thereon which alter, control and/or adjust the hydrophobic/hydrophilic properties of the surface of the underlying material. As surfaces of specific compositions or materials have their own specific characteristic properties including surface charge and those properties with respect to their affinity for different types of materials (e.g., hydrophobicity, hydrophilicity, oleophobicity and oleophilicity, as well as polar and non-polar attractiveness), it is often desirable to be able to provide treatments and coatings which can affect and/or alter those innate properties. These treatments can allow for broader use or improved use of the materials in differing environments. The basic process of that invention comprises applying a liquid coating onto a surface (e.g., a flat, shaped, irregular or particulate surface) having a relative property (e.g., of hydrophobicity), the liquid coating comprising, consisting essentially of, or consisting of a first compound having an inorganic oxidizable group or moiety, and then oxidizing said first compound to form a second compound which is bound to the surface, the second compound changing said relative property. In most cases this relative property will change to greater hydrophilicity, depending upon the essential nature of the first compound used. Preferred compounds comprise inorganic or more preferably metallic, metalloid or semimetallic ester containing compounds such as oxides $M_xO_y$ (as described above) and most preferably as silicon compounds such as silanes (e.g., $R_m Si[OR1]_n$), that is compounds wherein R is an organic group (preferably bonded to the Si atom through a carbon atom), halogen or hydrogen, R1 is H, or an organic group, such as alkyl, aryl or heterocycle, preferably alkyl of 1 to 4 carbon atoms, wherein m is 0, 1, 2 or 3 and n is 1, 2, 3 or 4; titanate counterparts of the silanes, such as $R_m Ti[O R1]_n$ in which R, R1, m and n are as defined above; and any other oxidizable metallo or semi-metallo compounds of the general formula $R_m M[R1]_n$ wherein M is a metal or semimetal such as those selected from the group consisting of Si, Ti, Zn, Al, Sn, Fe, Cu, Zr, B, Mg, Mn, W, Sb, Au, Ag, Cr, and the like, R and R1 are as defined above, m plus n equals the valence state of M, and n must be at least 1. In addition to the preferred silanes, mainly preferred because of their ease of use and ready commercial availability, silicon compounds such as silazanes, siloxane cyclics, siloxane dimers, siloxane trimers, silane fluids, and tris-(alkoxysiloxy)-3-methacryloxyalkylsilanes (less preferred) may be used in the practice of the present invention. In addition to these specific classes of compounds and metals/metalloids, and in addition to monometallic, monometalloid compounds as the starting materials, dimetallic (having two different metal/metalloid atoms, bimetallic (having two of the same metal/metalloid atoms in the compound), heterometallic (having one metal and one metalloid atom in the same compound), dimetalloid and bi-metalloid compounds, and mixtures of any of these groups of compounds are useful in the practice of the present invention. Mixtures and blends of the compounds provide unique capabilities for uniformly distributing different properties over a surface, or balancing (averaging) properties over the surface. An extremely wide range of these classes of oxidizable metal or metalloid compounds are commercially available, as exemplified by the lists of compounds in the 1996 Gelest, Inc. chemical catalog (e.g., pages 287 for a generic description of heterometallic and heterometalloid alkoxides, including alkali metal combinations; and especially pages 21–217; 220–221; 231–233; and 258–265) and the 1994 PCR, Incorporated General Catalog of "Chemicals for Research Scientists, especially pages 192–193 and 198–199). Germanium compounds have a functional similarity to silicon compounds in the practice of that invention.

BRIEF DESCRIPTION OF THE INVENTION

Liquids are stably encapsulated within a particulate 'shell' creating a pourable or flowable particle that can be easily disrupted to release the liquid with the possibility of minimal shell residue remaining. The encapsulated material may be both relatively stable (being able to be transported and poured without immediate breakage), yet may be easily broken apart to release the entrapped liquid. The particles exhibit a high degree of sphericity in both individual particles and in masses of particles.

An aqueous medium (i.e., a liquid medium comprising at least 5% by weight of water) is encapsulated in a 'shell' of particles that surround the liquid medium, preventing the liquid medium from directly contacting surfaces on the outermost surfaces of the capsules. The particles surrounding the liquid form a loose, confining outer dimension of material that prevents the liquid from directly contacting surfaces in contact with the confining particles. The confining particle 'shell' can be easily disrupted by pressure and abrasion, yet the capsulate can be easily transported and poured without releasing the entrapped liquid. Control of the effective porosity of the 'shell' can be effected by the selection of the size and distribution of particles in the confining particle shell.

DETAILED DESCRIPTION OF THE INVENTION

In the practice of the present invention, certain terms are used within their accepted broad meaning in the field, but have particular applicability to the practice of the invention, so their definition is warranted to assist in the appreciation of the invention.

There are basically three types of particles under discussion in the practice of the present invention, 1) the encapsulating or entrapping particles, 2) the encapsulated or product particles, and 3) the additive or supplemental particles. The first particles, the encapsulating or entrapping particles, are the particles that appear on the surface of liquid drops or droplets, and form a stabilizing shell or surface region around the liquid. These are also referred to as the hydrophobic particles, as the particles must have a hydrophobic surface to enable their being supported and retained on the surface of the aqueous droplets.

The second type of particle is an actual final or intermediate product of the present invention, referred to as an encapsulated system, encapsulated particle or simply product particle. This may comprise a distinct aqueous phase surrounded by entrapping particles on the surface of the aqueous phase. The product particles may have the encapsulating particles supported on the surface of an aqueous droplet, with little or no physical attraction or bonding between the entrapping particles. The entrapping particles may also be loosely or tightly bonded to each other, as by supplemental treatments during or after formation of the encapsulated system. For example, a liquid, polymerizable material or composition may be applied (e.g., sprayed) over the encapsulated system, and the polymerizable composition polymerized by available means (e.g., ambient moisture, thermal polymerization, radiation-induced polymerization, photoinitiation, or the like, as well understood in the art). An example of this would be the spraying or evaporative deposition of a neat solution of gamma-glycidoxypropyltrimethoxy silane with a triarylsulfonium hexafluoroantimonate photoinitiator (which is active towards both the epoxy functionality and the silane functionality in the presence of moisture).

Figure 3:
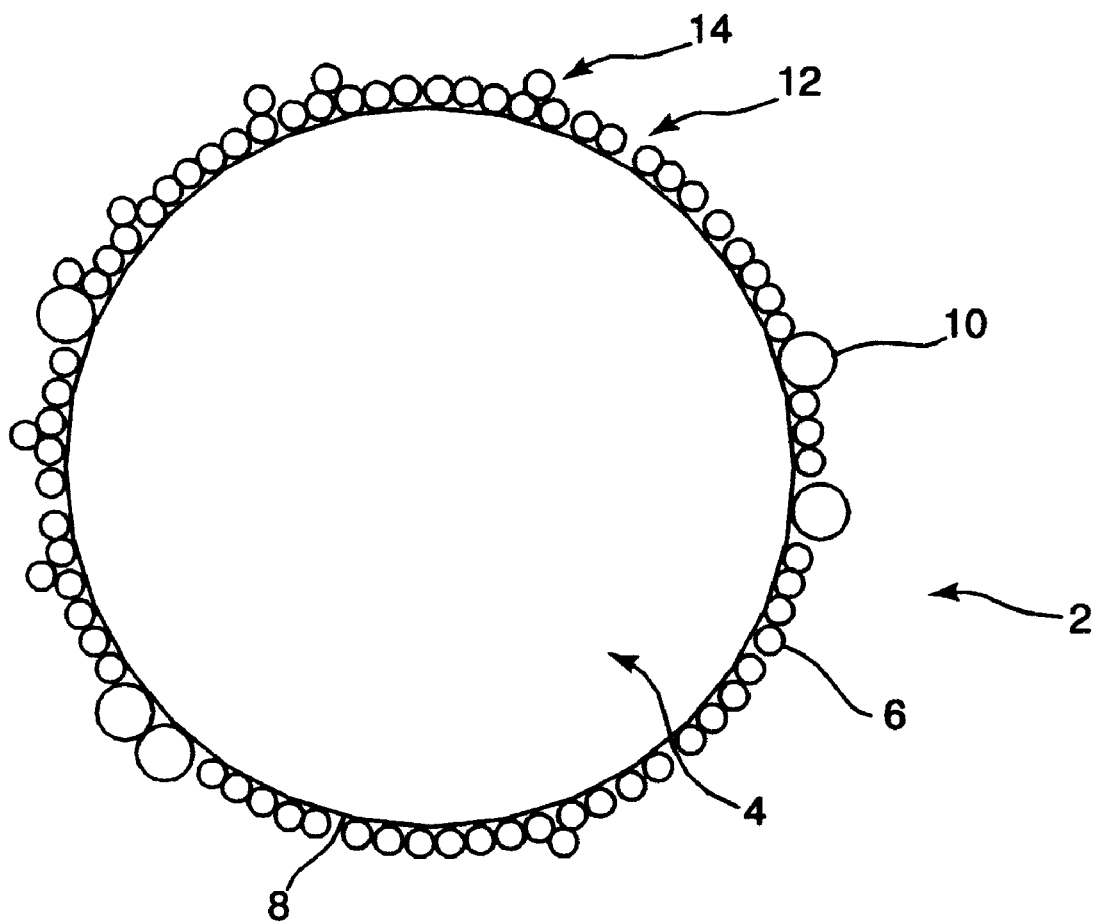
FIG. 3 shows a cross-section of an encapsulated liquid medium according to the present invention.

The third type of particles, the supplemental particles or additive particles, are merely particles of any type that are added to the encapsulated particles to provide additional or supplemental properties or material. These three types of particles can be viewed in FIG. 3, showing a cross-section of an encapsulated particle 2 of the present invention. The encapsulated particle 2 is shown as comprising a core 4 of aqueous medium, surrounded by entrapping particles 6. These entrapping particles may comprise various size particles such as shown with particles 6 and 10. The particles 6 and 10 will, according to natural distribution and packing phenomena, attempt to align themselves and cover the surface 8 of the aqueous core 4. Because of natural random phenomena and lack of absolute control, the entrapping particles 6 and 10 will not necessarily pack in perfectly organized diameters over the surface 8, but may allow for some spacing 12 between particles and, allow for some stacking 14 of particles, held together by inter-particle phenomena or by binding agents (not shown). Depending upon the strength of inter-particle attractions, there may even be partial or complete layers of particles 6 and 10 on the droplet core 4. It should be considered that FIG. 3 is a cross-section of an encapsulated particle system according to the present invention, and that the variations shown in FIG. 3 will also occur in three dimensions over the entire spherical surface of the core 4.

The term "low-energy mixing" is used to describe the control placed on the energy used to mix the encapsulating hydrophobic particles and the water droplets (e.g., the atomized spray of aqueous material) after they have been associated, but without previous formation of the encapsulated system. It is this low-energy mixing, as with a rotated bed of particles (e.g., in a rotating, non-bladed mixer, such as a small cement mixer) with the liquid atomized onto the surface of the particles before or during rotation of the bed. That quantified amount of energy for the "low energy mixing" is approximately within the range of a kinetic energy of the mixing system being typically from 0.00005 to 5.0 kg m$^2$ sec-1 (standard MKS units), preferably from 0.0005 to 1.0 kg m² sec-1, and more preferably between 0.005 and 0.1 kg m2 sec-1.

The particles are described according to their "Volume (or Mass) Mean Particle Diameter." This is a statistic of a particle size distribution that gives the mean particle diameter, weighted by volume. It is a term well understood and broadly used in the art of particle size analysis. Briefly, if all particles in a size distribution are put into equal size "bins" of increasing diameter, larger diameter particles will contribute a greater fraction of the volume (or equivalently, mass) to the total volume (or mass) of the distribution than will particles of smaller diameter. A volume weighted mean particle diameter is found by taking the product of the particle diameter and volume in each bin, and dividing this product by the total volume of the distribution. For more details, reference: Aerosol Technology, by William Hinds, John Wiley and Sons, 1982.

An encapsulation system according to the present invention may comprise a core of aqueous liquid having at least 5% by weight water therein, and an encapsulant surrounding the core to form stable encapsulated particles, the encapsulant comprising at least one layer of hydrophobic particles in contact with and surrounding the core, the core and hydrophobic particles providing an encapsulated system that has a volume weighted mean particle diameter of from 0.05 to 25 micrometers, at least 25% of the encapsulated particles are spherical and can support its own weight. The core may, for example, comprise an aqueous solution having a diameter of from 0.0001 to 1 mm, with a water content of from 10–98%, 10–95%, 10–90%, or 30–90% average percentage by weight of the encapsulation system. The hydrophobic particles may even comprise microcapsules, or the encapsulation system may be admixed (blended) with microcapsules. It is also desirable to have non-encapsulated particles admixed with the encapsulated particles into a multi-particulate system. A wide range of relative ingredients may be provided by the system, such as (for the system itself, and not including additive particles blended or admixed with the system) the water comprising from 40–98% percent by weight of said encapsulation system and said hydrophobic particles comprising from 2 to 60% by weight of said encapsulation system.

An alternative way of describing the invention is as an encapsulation system comprising droplet cores of aqueous liquids having diameters of from 0.0001 to 0.5 mm of aqueous liquid having a surface, the droplets having a stabilizing layer comprising hydrophobic particles with a volume weighted mean particle diameter of from 0.05 to 25 micrometer hydrophobic particles on the surface, the stabilizing layers being generally spherical, with at least 25% by number of all encapsulated particles in the encapsulated system having less than a 25% deviation in diameter in cross-sections of encapsulated particles. The hydrophobic particles may be totally unbonded to each other, partically bonded or entirely bonded to each other in the encapsulating layer, as with the layer of hydrophobic particles comprising a layer of particles with less than 80% by number of the particles being bonded to any adjacent particle, or at least 30% by number of hydrophobic particles in the layer of hydrophobic particles bonded to adjacent particles. The method for providing such stable encapsulant systems may comprise providing a mass of hydrophobic particles having average mass diameter size of between 0.05 and 25 micrometers, providing droplets of an aqueous medium to the mass of particles, gently mixing the fine particles of aqueous medium and the hydrophobic particles to form a stable encapsulant system of droplets of said aqueous medium encapsulated by a shell of particles. The method may have the mixing done at a low energy mixing rate of from 0.00005 to 5.0 kg m2 sec-1, or from 0.0005 to 1.0 kg m2 sec-1. The spraying and/or the mixing may be performed in the presence of at least one component present within the encapsulant system selected from the group consisting of pharmaceuticals, flavorings, vitamins, dyes, pigments, reactants, moisturizers, emollients, bleaching agents, whitening agents, lightening agents, darkening agents, radiation absorbing materials, reflective materials, catalysts/reactants, enzymes, pheromones, bioactive ingredients, inert materials, solutions of salts and oils. These materials, the additive particles, and other ingredients may be added to the materials being used to make the encapsulation system before addition of the small droplets of water, during the addition of the small droplets of water, after the addition of the water, before mixing, during mixing or the like. The additive particles may also be added to the encapsulated system after it has been formed. It is surprising that the encapsulated system may be formed in the presence of non-hydrophobic or hydrophobic additive particles and/or microcapsules that are not primary particles in the entrapping layer over the spherical liquid aqueous solution bead. The droplets may, for example, comprise an aqueous solution having an average droplet diameter of from 0.0001 mm to 1 mm, and within each encapsulated particle, the water may comprise 10–98%, 10–95%, 10–90%, 10–75% or 30–75% average percentage by weight of the encapsulation system, exclusive of additive particles or admixed material. A desirable mixing method is effected by a rotated bed/water atomization process. The treatment of the particles to enhance their hydrophobicity can be beneficial. This can be done with the already hydrophobic commercially available particles to increase their hydrophobicity. For example, where the hydrophobic particles comprise fumed silica, further chemical or electrochemical treatment may be used to form fumed silica particles having non-fumed reactive sites or non-fumed non-reactive sites that add to the hydrophobicity of a surface of the hydrophobic particles.

A hydrophobic particle is used to encapsulate aqueous materials by assuring that a shield of the particles is formed around the core of aqueous material. The hydrophobic particles may vary greatly in size, generally within a range of about 0.05 micrometers to 25 micrometers (volume average particle size), with the measurement of the size of the particles including both individual particle measurements and agglomerated particle measurements. As is well understood in the art, when particles are provided, either alone or in contact with a liquid medium (with even ambient moisture vapor being sufficient), the particles may exist as distinct and separable particles or may tend to agglomerate into virtually larger particles that themselves act as particles. This is usually a consideration in the determination of any measurement or limitation of 'particle size.' For example, individual particles of about 0.05 micrometers may remain as separate particles or may agglomerate into effective particles sizes (inelegantly referred to as "lumps" or "clumps") that are significantly larger, depending upon the number of individual particles that are associated into the effectively larger particles. In many instances, the agglomerated particles act as a unitary solid particle of the actual size of the agglomerate. When referring to "particles," "entrapping particles," "shell particles," "encapsulating particles" or the like, the term particles refers to both the individual particles and the agglomerated effective particles. The term "individual particles" or "agglomerated particles" is used to specifically and exclusively refer to a single classification of particles.

In conventional encapsulation systems, the material present in the center of the encapsulated system is referred to as the fill, or is alternatively referred to as the core and the surrounding wall is often referred to as the shell or the encapsulate. In the practice of the present invention, the term 'shell' has been heretofore quoted because of the unusual nature of the entrapping particles in the practice of the present invention. The individual or agglomerated entrapping particles may or may not be bonded to adjacent individual or agglomerated entrapping particles, depending upon the choice of the operator, circumstantial events, and the desired properties. The exact mechanism for the entrapping and stable arrangement of the particles is not fully understood, nor need be, as the specification enables the practice of the invention with all particles meeting the defined hydrophobic characteristics. However, in at least some circumstances, it is believed that the hydrophobic particles may be supported by the surface tension of the liquid medium, with no bonding between adjacent particles being necessary to support an encapsulated structure. The rigidity of the encapsulation may be adjusted by a number of means, including, but not limited to, control of the bonding of the particles around the liquid material, relative hydrophobicity of the particles and surface tension of the liquid, viscosity of the liquid, the polarity/non-polarity of the core and the entrapping particles, electrostatic charging of the liquid and the particles of the shell, and the like.

The encapsulated materials of the present invention may generically be provided in the following manner: hydrophobic particles of a volume weighted mean particle diameter from 0.05 to 25 micrometers are provided; a fine spray of aqueous material is provided to the hydrophobic particles; and the particles and liquid are gently agitated (e.g., tumbled), producing the encapsulated articles.

There are significant subtleties and variations that must be practiced to perform this process. For example, the hydrophobic particles must have a contact angle with deionized water at 20° C. of at least 70°, as that property is known to be measured. The higher the contact angle, the larger a droplet of liquid may be maintained within the encapsulation. Contact angles of at least 80°, at least 90°, at least 100°, at least 110°, at least 120°, and at least 130°, or more are particularly useful. The aqueous material must not reduce that contact angle significantly, although depending on the relative native contact angle of the particle surface and surface tension of the liquid, a wide range of materials may be combined. For example, distilled water has a surface tension of about 72 dynes/cm at 25° C., and 75 dynes/cm at 0° C. Aqueous materials with higher surface tension therefore can be used with the lower contact angle surfaces (e.g., contact angle of 70° material), while water with some mildly surfactant materials (reducing the surface tension to 60–65 dynes/cm) might desirably use a particle with a higher contact angle (e.g., 130°).

The size of the water or aqueous core may also vary over a wide range, again as indicated above, with the relative contact angle and surface tension being considered to enable larger size encapsulations to occur. Droplet sizes from about 0.01 to 1000 micrometers are believed to be sustainable, and a wide range of droplet sizes have been made and sustained in the practice of the present invention.

The particles used as the hydrophobic particles in the practice of the present invention do not have to be uniformly solid or uniformly dimensioned particles, but may be hollow particles, microcapsules, or blends of particles of various types and sizes. The primary controlling characteristics essential to the practice of the present invention are the property of hydrophobicity and the quality of size previously discussed (e.g., within about 0.05 to 25 micrometers in weight average particle size). It is this wide range of acceptability of particle characteristics and aqueous liquid characteristics that adds special benefits to the practice of the present invention. Extreme variations among materials may be provided in an effectively single component (the particulate entrapment system) system in the practice of the present invention. For example, the aqueous medium may provide water or aqueous solutions, aqueous dispersions, or aqueous emulsions (with care taken on the strength of emulsifying agents that could adversely affect the surface tension of the system). At the same time, the particulate entrapping material could provide diverse solid particulates (diverse in size, composition, or other properties), hollow particulates, encapsulated hydrophilic materials, or encapsulated hydrophobic materials within a microcapsule that had been treated to provide a hydrophobic surface. As the surface of the microcapsule could be treated to provide the needed hydrophobic property, substantially any material that can be coated or encapsulated could be provided in the particle entrapping layer surrounding the aqueous medium core.

In addition to the "entrapping particles" used in the practice of the present invention, supplemental or additive particles may be combined with the system of the present invention. That is, once the encapsulated system of the present invention has been manufactured, other particles may be combined therewith for addition to the composition or blended into a different supporting composition. These particles are not restricted by the size limitations of the entrapping particles. For example, calcium carbonate particles, titania particles or zinc oxide particles can be provided that are smaller than the limits of aqueous wettability and added to the composition. Similarly, poly (oxymethylene-urea) capsules can be both larger than the entrapping particles and the encapsulated system, are wettable, yet can be combined with the encapsulated system. Additional additive particles could include, by way of example only, polymers, resins, inorganics, organics, crystalline materials, amorphous materials, ceramics, glasses, clays, micas, salts, bioactives, pharmaceuticals, and the like, with merely exemplary size ranges of from 0.01 micrometers to 1000 micrometers as spheres, flakes, shaped particles, agglomerates, bubbles, and the like, with or without any hydrophilic or hydrophobic fill or coating.

Because of the ability to provide such diverse physical properties in the various components, a single system can deliver materials that ordinarily could not be provided from a single source. For example, combinations of materials that are either a) hydrophilic, hydrophobic, or ambiphilic, b) polar and non-polar, c) anionic and cationic, and/or d) oxidative and reductive could be provided from amongst such functional ingredients as pharmaceuticals, flavorings, vitamins, fragrances, colorants (dyes or pigments), solvents, reactants, moisturizers, emollients, bleaching agents, whitening agents, lightening agents, darkening agents, radiation (e.g., particularly UV) absorbing materials, reflective materials, catalysts/reactants, enzymes, pheromones, bioactive ingredients, inert materials, water, solutions of salts, oils, etc. Many of these materials could not have been previously provided in a single stable system where both materials could be readily released prior to the present invention. These encapsulated systems may be stored for months or years in some cases, and then when rubbed, release the liquid. Because the encapsulating particles are small (even when agglomerated into an effectively larger particle), they break up into the smallest particle size easily, or the shells fragment into smaller pieces, leaving average size particles that are not easily sensed (e.g., felt or seen) by the user.

Microcapsules useful in the present invention may be made by a wide variety of processes. These varied processes provide different techniques for producing capsules of varying sizes, alternative materials for the composition of the capsule shell and various materials within the shell. Some of these various processes are shown in U.S. Pat. Nos. 3,516,846; 3,516,941; 3,778,383; 4,087,376; 4,089,802; 4,100,103 and 4,251,386 and British Pat. Specification Nos. 1,156,725; 2,041,319 and 2,048,206. A wide variety of different materials may also be used in making the capsule shells. Popular materials for shell formation are the polymerization reaction products between urea and formaldehyde or melamine and formaldehyde, or the polycondensation products of monomeric or oligomeric polymers of dimethylolurea or methylolated urea with aldehydes. A variety of capsule forming materials are disclosed, for example, in U.S. Pat. Nos. 3,516,846 and 4,087,376 and U.K. Patent Specification Nos. 2,006,709 and 2,062,570. Preferred microcapsules may be found in Matson, U.S. Pat. No. 3,576,941.

One method of adjusting the hydrophobicity of the surface of particles used in the practice of the present invention is the method of U.S. Pat. No. 6,045,650, which is incorporated herein by reference for its procedures and materials used in those procedures. Those materials, in addition to those silanes and titanates, including those mentioned above, include at least compounds with active groups on metals/metalloids, monometallic, monometalloid compounds as the starting materials, dimetallic (having two different metal/metalloid atoms, bimetallic (having two of the same metal/metalloid atoms in the compound), heterometallic (having one metal and one metalloid atom in the same compound), dimetalloid and bi-metalloid compounds, and mixtures of any of these groups of compounds are useful in the practice of the present invention. Mixtures and blends of the compounds provide unique capabilities for uniformly distributing different properties over a surface, or balancing (averaging) properties over the surface. An extremely wide range of these classes of oxidizable metal or metalloid compounds are commercially available, as exemplified by the lists of compounds in the 1996 Gelest, Inc. chemical catalog (e.g., pages 287 for a generic description of heterometallic and heterometalloid alkoxides, including alkali metal combinations; and especially pages 21–217; 220–221; 231–233; and 258–265) and the 1994 PCR, Incorporated General Catalog of "Chemicals for Research Scientists, especially pages 192–193 and 198–199). Germanium compounds have a functional similarity to silicon compounds in the practice of the present invention. A wide range of these compounds, as shown in the 1996 Gelest, Inc. catalog identified above, as shown particularly on pages 216–217.

Similarly, as indicated above, oxidizable tin compounds are another class of compounds useful equivalently to the silicon compounds preferred in the practice of the present invention. There are many commercially available alternatives within this class, as shown for example on pages 258–264 of the 1996 Gelest, Inc. chemical catalog. Examples of R (as shown in the silicon compound formula above, and equally applicable in corresponding groups attached to other metal or metalloid atoms in the oxidizable compounds of the present invention) are apparent to those of ordinary skill in the art and they may be functional (e.g., specifically reactive) groups or relatively non-reactive groups which may provide useful physical properties when the material is deposited on the surface prior to oxidation, or less likely, leave a residue which is advantageous after oxidation. Such R groups would include aliphatic and aromatic groups such as alkyl groups, alkyl ester groups, poly(oxyalkylene) groups, phenyl groups, naphthyl groups, H, hetero groups (e.g., thioethers), functionally terminated groups such as amino-alkyl, epoxy-alkyl, carboxyalkyl, even possibly halogen atoms such as I, Br, Cl and F (but these are much less preferred because of the halogen products, including halogenic acids) and the like. $R^1$ may be any oxidizable group such as an ester group, including those with their own functionality on the distal (from the position of attachment) end of the group. Such groups $R^1$ after attachment form ester or ester type groups so that $R^1$ is actually an aliphatic or aromatic group such as R, but is preferably limited to aliphatic groups of 1 to 20 carbon atoms, more preferably 1 to 10 carbon atoms, and most preferably 1 to 4 carbon atoms for aliphatic groups and 1 to 10 carbon atoms for aromatic groups. For silicon based compounds, representative examples are the silicone compounds described in U.S. Pat. No. 5,486,631, the reactive silanes of U.S. Pat. No. 4,084,021 and many other commercially available silicon compounds which may be oxidized, particularly at temperatures between 250 to 600° C., and more particularly at temperatures between 350 and 500° C. It is also possible to use low temperature oxidizing environments, such as with oxidizing additives present or oxidizing vapor conditions, or with aerobically carried catalysts or accelerants to enable lower temperature oxidation onto surfaces which ordinarily could not withstand the temperatures used to oxidize the silicon containing materials (or other classes of materials). The oxidation product of this reaction may actually create a direct chemical bond to the composition of the substrate, or may merely create strong physical attachments, but the former appears to be the more likely result based on washing of the surfaces after the oxidation process.

The other classes of compounds include the counterparts of these compounds (i.e., with the silicon replaced by the other elements) such as titanate esters, zirconium esters, and other metal or non-metal esters. Mixtures of the various oxidizable compounds may be used, as suggested above, with particularly beneficial results, providing variations or mixtures of properties on surfaces, discontinuous areas of specific properties, blends (averages of properties), and the like.

A non-exhaustive list of compounds useful within the practice of the present invention includes such materials as:

Isobutyltrimethoxysilane, Aminopropyltriethoxysilane, Aminopropyltriethoxysilane, 3-Methacryloxypropyl-trimethoxysilane, n-(2-Aminoethyl)-3-amino-propyltrimethoxysilane,
3-Glycidoxypropyltrimethoxysilance,
n-Octyltriethoxysilane, Hexamethyldisilazane,
Diethylsilane, Vinyldimethylchlorosilane,
Vinylmethyldichlorosilane,
Vinylmethyldimethoxysilane, Tetrakis[1-methoxy-2-propoxy]silane, Triethylchlorosilane,
Vinylmethyldiethoxysilane, Vinyltrichlorosilane,
Vinyltrimethoxysilane, Vinyltriethoxysilane,
Dimethyldiethoxysilane, Hexamethyldisilazane,
Divinyltetramethyldisilazane, Tetramethyldisilazane,
Heptamethyldisilazane, Tris[(trifluoropropyl)methyl] cyclotrisiloxane, Methylvinylcyclotetrasiloxane, 1,3,5, 7-Tetramethylcyclotetrasiloxane, 1,3,5,7,9-Pentamethylcyclopentasiloxane,
Hexamethyldisiloxane, Divinyltetramethyldisiloxane,
Divinyltetramethyldisiloxane (high Purity), Tetramethyldisiloxane, 1,3-Bis(3-aminopropyl) tetramethyldisiloxane, Heptamethyltrisiloxane, Chlorinated phenyl methyl polysiloxane, 1,3Bis(aminopropyl)tetramethyldisiloxane, Bis(3-aminopropyl)polydimethylsiloxane, Bis(3-aminopropyl)polydimethylsiloxane, Diethoxy polydimethylsiloxane, Tris(trimethylsiloxy)3-mehtacryloxypropylsilane, Tetraisopropoxygermane, Tetrakis(Trimethylsiloxy-Germane, Tetramethoxygermane, Tetramethylgermane, Tetrapentylgermane, Tetraphenylgermane, Tetra-n-Propylgermane, Tetra-p-Tolylgermane, Triallylfluorogermane, Tri-n-Butylacetoxygermane, Tetraphenyltin, Tetravinyltin, Tetraphenltin Tetravinyltin, Tin II Acetate, Tin IV Acetate, Tin Acetylacetonate, Tin t-Butoxide, Tin II Chloride, anhydrous Tin II Chloride, Dihydrate Tin IV Chloride, anhydrous Tin II Ethoxide, Tin II Flouride, Tetramethyltin, Tetra-n-Octyltin, Tetra-n-Pentyltin, Tetraethyltin, Tetraisopropoxytin-Isopropanol Adduct, Tetraisopropyltin, Tetrakis(Diethylamino)Tin, Tetrakis(Dimethylamino)Tin, Potasium Stannate trihydrate, Sodium Stannate trihydrate, Sodium Tin Ethoxide, Stannic Chloride, Tetraacetoxytin, Tetraallyltin, Tetra-t-Butoxytin, Tetra-n-Butyltin, Methacryloxytri-n-Butyltin, Methyltrichilorotin, Phenylethynyltri-n-Butyltin, Phenyltri-n-Butyltin, Phenyltrichlorotin, Divinyldi-n-Butyltin, 1-Ethoxyvinyltri-n-Butyltin, Ethynyltri-n-Butyltin, Hexabutyldistannoxane, Hex-n-Butylditin, Hexamethylditin, Dimethylhydroxy (Oleate)Tin, Dimethyltin Oxide, Dioctyldichlorotin, Dioctyldilauryltin, Dioctyldineodecanoatetin, Dioctyl (Maleate)Tin, Dioctyltin Oxide, Diphenyldichlorotin, Allytrichlorogermane, Allyltriethylgermane, Allytrimethylgermane, 3-Aminopropyltributylgermane, Ammonium Hexafluorogermanate, Ammonium Tris(Oxalato) Germanate, Benzyltricholorogermane, Bis[Bis(Trimethylsilyl)Amino]-Germanium II, Bis(Chloromethyl)Dimethylgermane, Bismuth Germanate, Bromomethyltribormogermane, Bromotrimethylgermane, Tetra-n-Butylgermane, Tetraethoxygermane, and Tetraethylgermane.

Preferred silicon compounds of the present invention may be represented by the formula: Me—$(CH2)_a$Si—$(OR)_3$ wherein Me is a methyl group, R is an organic group, preferably an alkyl group having one to ten carbon atoms, R is an alkyl or aryl group, preferably a methyl or ethyl group, and a is an integer within the range of 0 to 12. Counterparts of these materials where Me is replaced with other organic groups, particularly alkyl groups are useful in the practice of the present invention, as are the other nominative elemental counterparts (e.g., the titania, germainum, etc. counterparts of silicon).

As used in the practice of the present invention, it is well understood that the art tolerates or even advises on substitution of groups within these chemical formulae. To that end, wherever the term "group" is used in described a chemical material or functionality, conventional substitution is specifically included within the description of that term. For example, where alkyl group is recited, not only are alkyl moieties such as methyl, ethyl isobutyl, t-butyl, iso-octyl, and dodecyl included, but also alkyls with such conventional substitution as is recognized within the relevant art, such as hydroxymethyl, 1-, or 2-halo-ethyl, omega-cyano-butyl, propyl-sulfonate, etc. with such substituent groups as amino, carboxyl, acyl, etc. tolerated according to the general practices of the art. Where the term "moiety" is used, as in alkyl moiety, that term reflects only the strict definition of alkyl (or other moiety modified group) without allowance for substitution.

The particulate substrates onto which the compositions of the invention may be deposited and oxidized into coatings are essentially limited only by the ability of the substrate to be resistant to the temperatures used in the oxidation process. Metal, metal oxide, inorganic oxides generally, glasses, ceramics, composites, pigments (organic or inorganic), lakes, catalysts, reflective particles, magnetic particles, radiation absorbing particles, flat surfaces, shaped surfaces, structural elements and the like may all take advantage of the compositions and process of the present invention. Because the composition of the invention may be readily controlled as to the thickness or continuity of the final coating, a wide range of other uses and properties may be provided. For example, by controlling the amount of liquid coating on the surface, the continuity of the liquid coating, the thickness of the liquid coating, and the like, similar attributes in the final oxidized materials may also be controlled. If the coated substrate were catalytic in nature, the degree of porosity allowed in the coating could control the degree of exposure of the catalyst. If the underlying substrate were highly hydrophobic, the specific degree of hydrophilicity/hydrophobicity of the product could be controlled by designing the specific percentage of the surface to be the exposed underlying material or the coating produced by the oxidation process. In addition to these specific classes of compounds and metals/metalloids, and in addition to monometallic, monometalloid compounds as the starting materials, dimetallic (having two different metal/metalloid atoms, bimetallic (having two of the same metal/metalloid atoms in the compound), heterometallic (having one metal and one metalloid atom in the same compound), dimetalloid and bi-metalloid compounds, and mixtures of any of these groups of compounds are useful in the practice of the present invention. Mixtures and blends of the compounds provide unique capabilities for uniformly distributing different properties over a surface, or balancing (averaging) properties over the surface. An extremely wide range of these classes of oxidizable metal or metalloid compounds are commercially available, as exemplified by the lists of compounds in the 1996 Gelest, Inc. chemical catalog (e.g., pages 287 for a generic description of heterometallic and heterometalloid alkoxides, including alkali metal combinations; and especially pages 21–217; 220–221; 231–233; and 258–265) and the 1994 PCR, Incorporated General Catalog of "Chemicals for Research Scientists, especially pages 192–193 and 198–199). Germanium compounds have a functional similarity to silicon compounds in the practice of the present invention. A wide range of these compounds, as shown in the 1996 Gelest, Inc. catalog identified above, as shown particularly on pages 216–217.

Similarly, as indicated above, oxidizable tin compounds are another class of compounds useful equivalently to the silicon compounds preferred in the practice of the present invention. There are many commercially available alternatives within this class, as shown for example on pages 258–264 of the 1996 Gelest, Inc. chemical catalog. Examples of R (as shown in the silicon compound formula above, and equally applicable in corresponding groups attached to other metal or metalloid atoms in the oxidizable compounds of the present invention) are apparent to those of ordinary skill in the art and they may be functional (e.g., specifically reactive) groups or relatively non-reactive groups which may provide useful physical properties when the material is deposited on the surface prior to oxidation, or less likely, leave a residue which is advantageous after oxidation. Such R groups would include aliphatic and aromatic groups such as alkyl groups, alkyl ester groups, poly(oxyalkylene) groups, phenyl groups, naphthyl groups, H, hetero groups (e.g., thioethers), functionally terminated groups such as amino-alkyl, epoxy-alkyl, carboxyalkyl, even possibly halogen atoms such as I, Br, Cl and F (but these are much less preferred because of the halogen products, including halogenic acids) and the like. R.sup.1 may be any oxidizable group such as an ester group, including those with their own functionality on the distal (from the position of attachment) end of the group. Such groups $R^1$ after attachment form ester or ester type groups so that $R^1$ is actually an aliphatic or aromatic group such as R, but is preferably limited to aliphatic groups of 1 to 20 carbon atoms, more preferably 1 to 10 carbon atoms, and most preferably 1 to 4 carbon atoms for aliphatic groups and 1 to 10 carbon atoms for aromatic groups. For silicon-based compounds, representative examples are the silicone compounds described in U.S. Pat. No. 5,486,631, the reactive silanes of U.S. Pat. No. 4,084,021 and many other commercially available silicon compounds which may be oxidized, particularly at temperatures between 250 to 600° C., and more particularly at temperatures between 350 and 500° C. It is also possible to use low temperature oxidizing environments, such as with oxidizing additives present or oxidizing vapor conditions, or with aerobically carried catalysts or accelerants to enable lower temperature oxidation onto surfaces which ordinarily could not withstand the temperatures used to oxidize the silicon containing materials (or other classes of materials). The oxidation product of this reaction may actually create a direct chemical bond to the composition of the substrate, or may merely create strong physical attachments, but the former appears to be the more likely result based on washing of the surfaces after the oxidation process.

The other classes of compounds include the counterparts of these compounds (i.e., with the silicon replaced by the other elements) such as titanate esters, zirconium esters, and other metal or non-metal esters. Mixtures of the various oxidizable compounds may be used, as suggested above, with particularly beneficial results, providing variations or mixtures of properties on surfaces, discontinuous areas of specific properties, blends (averages of properties), and the like.

A non-exhaustive list of compounds useful within the practice of the present invention includes such materials as:
Isobutyltrimethyoxysilane, Aminopropyltriethoxysilane, Aminopropyltriethoxysilane, 3-Methacryloxypropyl-trimethoxysilane, n-(2-Aminoethyl)-3-aminopropyltrimethoxysilane, 3-Glycidoxypropyltrimethoxysilance, n-Octyltriethoxysilane, Hexamethyldisilazane, Diethylsilane, Vinyldimethylchlorosilane, Vinylmethyldichlorosilane, Vinylmethyldimethoxysilane, Tetrakis[1-methoxy-2-propoxy]silane, Triethylchlorosilane, Vinylmethyldiethoxysilane, Vinyltrichlorosilane, Vinyltrimethoxysilane, Vinyltriethoxysilane, Dimethyldiethoxysilane, Hexamethyldisilazane, Divinyltetramethyldisilazane, Tetramethyldisilazane, Heptamethyldisilazane, Tris[(trifluoropropyl)methyl]cyclotrisiloxane, Methylvinylcyclotetrasiloxane, 1,3,5, 7-Tetramethylcyclotetrasiloxane, 1,3,5,7,9-Pentamethylcyclopentasiloxane, Hexamethyldisiloxane, Divinyltetramethyldisiloxane, Divinyltetramethyldisiloxane (high Purity), Tetramethyldisiloxane, 1,3-Bis(3-aminopropyl) tetramethyldisiloxane, Heptamethyltrisiloxane, Chlorinated phenyl methyl polysiloxane, 1,3Bis (aminopropyl)tetramethyldisiloxane, Bis(3-aminopropyl)polydimethylsiloxane, Bis(3-aminopropyl)polydimethylsiloxane, Diethoxy polydimethylsiloxane, Tris(trimethylsiloxy)3-mehtacryloxypropylsilane, Tetraisopropoxygermane, Tetrakis(Trimethylsiloxy-Germane, Tetramethoxygermane, Tetramethylgermane, Tetrapentylgermane, Tetraphenylgermane, Tetra-n-Propylgermane, Tetra-p-Tolylgermane, Triallylfluorogermane, Tri-n-Butylacetoxygermane, Tetraphenyltin, Tetravinyltin, Tetraphenltin Tetravinyltin, Tin II Acetate, Tin IV Acetate, Tin Acetylacetonate, Tin t-Butoxide, Tin II Chloride, anhydrous Tin II Chloride, Dihydrate Tin IV Chloride, anhydrous Tin II Ethoxide, Tin II Flouride, Tetramethyltin, Tetra-n-Octyltin, Tetra-n-Pentyltin, Tetraethyltin, Tetraisopropoxytin-Isopropanol Adduct, Tetraisopropyltin, Tetrakis(Diethylamino)Tin, Tetrakis (Dimethylamino)Tin, Potasium Stannate trihydrate, Sodium Stannate trihydrate, Sodium Tin Ethoxide, Stannic Chloride, Tetraacetoxytin, Tetraallyltin, Tetra-t-Butoxytin, Tetra-n-Butyltin, Methacryloxytri-n-Butyltin, Methyltrichilorotin, Phenylethynyltri-n-Butyltin, Phenyltri-n-Butyltin, Phenyltrichlorotin, Divinyldi-n-Butyltin, 1-Ethoxyvinyltri-n-Butyltin, Ethynyltri-n-Butyltin, Hexabutyldistannoxane, Hex-n-Butylditin, Hexamethylditin, Dimethylhydroxy (Oleate)Tin, Dimethyltin Oxide, Dioctyldichlorotin, Dioctyldilauryltin, Dioctyldineodecanoatetin, Dioctyl (Maleate)Tin, Dioctyltin Oxide, Diphenyldichlorotin, Allytrichlorogermane, Allyltriethylgermane, Allytrimethylgermane, 3-Aminopropyltributylgermane, Ammonium Hexafluorogermanate, Ammonium Tris(Oxalato) Germanate, Benzyltricholorogermane, Bis[Bis (Trimethylsilyl)Amino]-Germanium II, Bis (Chloromethyl)Dimethylgermane, Bismuth Germanate, Bromomethyltribormogermane, Bromotrimethylgermane, Tetra-n-Butylgermane, Tetraethoxygermane, and Tetraethylgermane.

Preferred silicon compounds of the present invention may be represented by the formula:

RSi(O R1)<sub>3</sub> wherein R1 is an organic group, preferably an alkyl group having one to ten carbon atoms, and R is an alkyl or aryl group, preferably a methyl or ethyl group. Counterparts of these materials where Si is replaced with other elements, particularly as other nominative elemental counterparts (e.g., the titania, germainum, etc. counterparts of silicon).

As used in the practice of the present invention, it is well understood that the art tolerates or even advises on substitution of groups within these chemical formulae. To that end, wherever the term "group" is used in described a chemical material or functionality, conventional substitution is specifically included within the description of that term. For example, where alkyl group is recited, not only are alkyl moieties such as methyl, ethyl isobutyl, t-butyl, iso-octyl, and dodecyl included, but also alkyls with such conventional substitution as is recognized within the relevant art, such as hydroxymethyl, 1-, or 2-halo-ethyl, omega-cyano-butyl, propyl-sulfonate, etc. with such substituent groups as amino, carboxyl, acyl, etc. tolerated according to the general practices of the art. Where the term "moiety" is used, as in alkyl moiety, that term reflects only the strict definition of alkyl (or other moiety modified group) without allowance for substitution.

Figure 1:
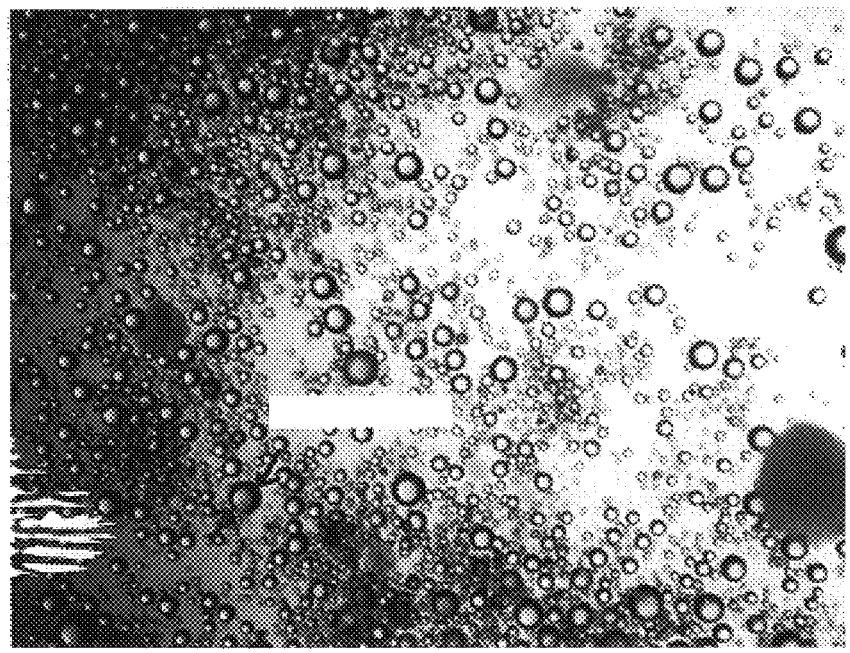
FIG. 1 shows a distribution of water encapsulated by hydrophobic particles according to a practice of the present invention, comprising 90% water and 10% silica.
Figure 2:
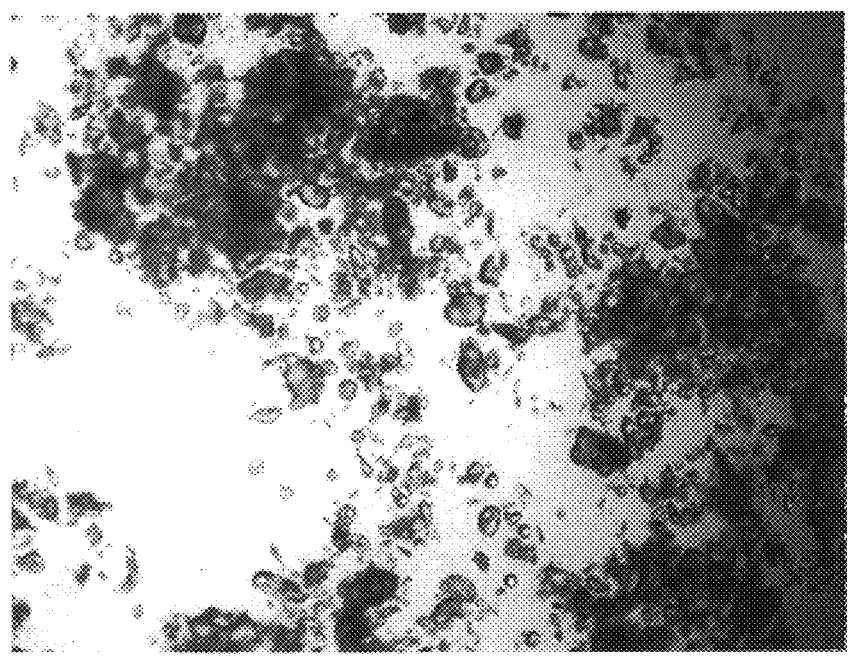
FIG. 2 shows the results of an attempt to form water surrounded by hydrophobic particles by methods other than those practiced in the present invention, believed to be manufactured according to U.S. Pat. No. 5,342,597 with the same percentage of water and the same silica.

Another attribute that appears to be unique to the practice of the present invention is the ability to produce encapsulated systems with a high degree of sphericity. Although microcapsules with a solid shell have provided high degrees of regular spherical appearance in encapsulated materials, there has heretofore been no known product with a liquid core and a multi-particulate shell with a high degree of sphericity. Looking for example at FIGS. 1 and 2, one aspect of uniqueness for the present invention can be appreciated. FIG. 1 shows a copy of a microscopic photograph of an unfiltered distribution of an encapsulated system according to the present invention. In the FIG. 1, an aqueous system of greater than 70% by weight water, less than 25% by weight butylenes glycol, and less than 10% by weight of hydrophobic fumed silica particles having a volume weighted mean particle diameter of between about 0.1 to 0.5 micrometers, the encapsulated particle system has a very high degree of sphericity. Not only are a large number percentage of the encapsulated particles (at least 20% by number, at least 25% by number, at least 40% by number, at least 50% by number, at least 60% by number, at least 75% by number, at least 80% by number, at least 90% by number, or at least 95% by number) spherical, but also the individual particles show a high spherical conformation. That is, large number percentages (as defined above) of the individual particles have regular diameters, indicative of true sphericity. That is, with the individual encapsulated particles, the diameters of the particles often may vary by less than 25%, less than 20%, less than 15%, less than 10% or less than 5% when the diameter is measured at different angular rotations across the particle. That is, as the encapsulated particle is rotated about its geometric center, the diameter appears to remain the same, with little asphericity, oval distortion, or other deviations from sphericity. The particles of FIG. 2 were asserted to have been made by brief but rapid sheering in a blender of a mixture of an aqueous solution and hydrophobic fumed silica particles. As can be seen from the comparison of the two FIGS. 1 and 2, there is little uniformity in the encapsulated particle system of FIG. 2, few encapsulated particles are spherical to any degree, there appears to be likelihood of reduced capability of large volumes of fill support, and the particle system itself would have an increased likelihood of agglomerating or packing at necks when poured because of the sharp features on the encapsulated particles. FIG. 2 shows beads that are believed to be manufactured by the process of U.S. Pat. No. 5,342,597, asserting that a dispersion of water in silica particles is provided, as opposed to a uniform and spherical coating of silica over water (or aqueous solution) droplets. The uniformity and control of the size and stability of encapsulated water (or aqueous solution) droplets according to the present invention provides significant differences and advantages to the practice of the present invention. Properties between encapsulated particles tend to be more uniform, the blending capability and pouring capability is enhanced because of the regular spherical shapes, the 'shells' may be more securely attached by bonding of particles (if desired), and additional ingredients may be added into a solid phase of these encapsulated particles.

The particles used in the practice of the present invention may be provided by a vast number of means and sources. Hydrophobic particles such as fumed silica may be purchased commercially or manufactured. Convenient manufacture would be by physical or sonic milling of larger particles (e.g., ball milling, hammer milling, sonic milling, jet milling and the like). These resultant smaller particles (milling reduces the size of particles in general) may then be treated with a hydrophobizing treatment such as those known in the art and as described above. Multiple treatments may be used, as where fumed silica (which has already been treated to increase hydrophobicity) is used with one or more additional treatment processes (e.g., those of U.S. Pat. No. 6,046,650 described above). Any treatment(s) that enable the particles to have a surface hydrophobicity as described above for the practice of the present invention will be suitable for use herein.

The oil may comprise esters of the formula RCO—OR' wherein R and R' are each independently a C1–25, preferably a C4–20 straight or branched chain alkyl, alkenyl or alkoxycarbonylalkyl or alkylcarbonyloxyalkyl. Examples of such esters include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, and fatty alcohols such as oleyl alcohol, isocetyl alcohol, and the like, as well as the esters disclosed on pages 24–26 of the C.T.F.A. Cosmetic Ingredient Handbook, First Edition, 1988, which is hereby incorporated by reference. The oil may also comprise glyceryl esters of fatty acids, or triglycerides, such as castor oil, lanolin oil, triisocetyl citrate, C.sub.10–18 triglycerides, caprylic/capric/triglycerides, coconut oil, corn oil, cottonseed oil, linseed oil, mink oil, olive oil, palm oil, illipe butter, rapeseed oil, soybean oil, sunflower seed oil, walnut oil, and the like.

Also suitable as the oil are glyceryl esters (excluding fats and oils which are glyceryl esters of fatty acids) which are primarily fatty acid mono-di- and triglycerides which are modified by reaction with other alcohols, for example, acetylated castor oil, glyceryl stearate, glyceryl dioleate, glyceryl distearate, glyceryl trioctanoate, glyceryl distearate, glyceryl linoleate, glyceryl myristate, glyceryl isostearate, PEG castor oils, PEG glyceryl oleates, PEG glyceryl stearates, PEG glyceryl tallowates, and so on. Also suitable as the oil are nonvolatile hydrocarbons such as isoparaffins, hydrogenated polyisobutene, mineral oil, squalene, petrolatum, and so on. Also suitable as the oil are various lanolin derivatives such as acetylated lanolin, acetylated lanolin alcohol, and so on.

Nonvolatile nonfluorinated silicones are also suitable as the oil component. Such silicones preferably have a viscosity of 10 to 600,000 centistokes, preferably 20 to 100,000 centistokes at 25° C. Suitable silicones include amodimethicone, bisphenylhexamethicone, dimethicone, dimethicone copolyol, dimethiconol, hexadecyl methicone, hexamethyldisiloxane, methicone, phenyl trimethicone, simethicone, dimethylhydrogensiloxane, stearoxy dimethicone, stearoxytrimethylsilane, vinyldimethicone, and mixtures thereof. Such silicones are available from Dow Coming as the 3225C formulation aid, Dow 190 and 193 fluids, or similar products marketed by Goldschmidt under the ABIL tradename. Also suitable as the oil are various fluorinated oils such as fluorinated silicones or perfluropolyethers. Particularly suitable are fluorosilicones such as trimethylsilyl endcapped fluorosilicone oil, polytrifluoropropylmethylsiloxanes, and similar silicones such as those disclosed in U.S. Pat. No. 5,118,496 which is hereby incorporated by reference. The nonvolatile component may comprise mixtures of fluorosilicones and dimethylpolysiloxanes. The nonvolatile component may also comprise perfluoropolyethers like those disclosed in U.S. Pat. Nos. 5,183,589, 4,803,067, 5,183,588 all of which are hereby incorporated by reference. These perfluoropolyethers are commercially available from Montefluos under the trademark Fomblin. Other suitable oils include sorbitan derivatives such as PEG sorbitan beeswax, PEG sorbitan isostearate, PEG sorbitan lanolate, PEG sorbitan laurate, PEG sorbitan oleate, PEG sorbitan palmitate, PEG sorbitan stearate, polysorbates, sorbitan trioleates, sorbitan sesquioleates, sorbitan stearates, sorbitan tristearates, and so on.

Pigments and Powders

The composition of the invention may contain 5–50%, preferably 7–45%, more preferably 10–40%, by weight of the total composition, of dry particulate matter having a particle size of 0.02 to 200, preferably 0.5 to 100, microns. The particulate matter may be colored or non-colored (for example white). Suitable powders include bismuth oxychloride, titanated mica, fumed silica, spherical silica, polymethylmethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof. The above mentioned powders may be surface treated with lecithin, amino acids, mineral oil, silicone oil or various other agents either alone or in combination, which coat the powder surface and render the particles more lipophilic in nature.

The powder component also may comprise various organic and inorganic pigments. The organic pigments are generally various aromatic types including azo, indigoid, triphenylmethane, anthraquinone, and xanthine dyes which are designated as D&C and FD&C blues, browns, greens, oranges, reds, yellows, etc. Organic pigments generally consist of insoluble metallic salts of certified color additives, referred to as the Lakes, in particular the Lakes of D&C and FD&C colors. Inorganic pigments include iron oxides, ultramarines, chromium, chromium hydroxide colors, and mixtures thereof. Preferably the composition will contain both pigment and non-pigmented powders. Obviously the percentage of pigments used in the powder component will depend on the type of cosmetic being formulated. Color cosmetics generally have a much higher concentration of color than other types of cosmetics. Generally the weight ratio of pigment to non-pigmented powder will range from 1:20 to 20:1.

The following, non-limiting examples are provided to exemplify and not limit the scope of practice of the present invention. The materials and conditions described therein are merely exemplary and evidentiary of the best mode of practicing the invention contemplated by the inventors.

EXAMPLES

Example 1

| | |
|---|---|
| TG-709 F Silica, milled to 0.3 microns | 3% |
| Water | 75.5 |
| 1,3-butane diol | 7 |
| PMU (polymelamine urea) fragrance capsules | 10 |
| Magnesium ascorbyl phosphate | 3 |
| Sodium Citrate | 1 |
| Methyl gluceth 10 | 0.5 |

Example 2

| | |
|---|---|
| TG-709 F Silica, milled to 0.3 microns | 3% |
| Water | 85.5 |
| 1,3-butane diol | 7 |
| Magnesium ascorbyl phosphate | 3 |
| Sodium Citrate | 1 |
| Methyl gluceth 10 | 0.5 |

Example 3

| | |
|---|---|
| TG-709 F Silica (unmilled), treated with SunSmart's SilubeTM-MT | 3% |
| Water | 90 |
| 1,3-butane diol | 7 |

Example 4

| | |
|---|---|
| TG-709 F Silica (unmilled) | 3% |
| Water | 90 |
| glycerin | 7 |

Each of these compositional examples was manufactured in approximately the same manner. A mass of the hydrophobic particles is provided into a tumbler, and other non-miscible ingredients were added to the mass of particles. (NOTE: one can either add the water soluble particles to the hydrophobic particles or first dissolve it in the water.) In all of these examples, the magnesium ascorbyl phosphate and the sodium citrate, if in the formula, were dissolved in the water. Water or the aqueous solution (the 1,3-butane diol, methyl gluceth 10, and glycerin are all liquids at room temperature and must be part of the aqueous phase in these examples) is atomized and sprayed onto the surface of the mass of particles in various sizes of water droplets (e.g., 0.1 to 1000 microns) while the hydropobic silca was being tumbled. (NOTE: the encapsulation occurs at the time of the spraying. Tumbling ends as soon as the spraying is completed). Without any further treatment, this encapsulated system could be poured, was flowable, was self-sustaining, and relatively stable. Because of the unbonded particulate coating over the water bead interior of the encapsulated particle system, storage of the beads in an air-tight container was desirable to reduce evaporation of water from the system. The process was performed at room temperature and pressure, although those conditions could be varied depending upon the properties of the various components, as where higher pressure would be desired to affect relative solubility or volatility of components, and temperature variations could be similarly used or used to control viscosity.

What is claimed:

1. A spherical encapsulation system comprising a core of aqueous liquid having at least 5% by weight water therein, and an encapsulant surrounding the core to form stable encapsulated particles, the encapsulant comprising at least one layer of hydrophobic particles in contact with and surrounding the core, the core and hydrophobic particles providing an encapsulated system that has a volume weighted mean particle diameter of from 0.05 to 25 micrometers, at least 25% of the spherical encapsulated system is spherical and can support its own weight.

2. The encapsulation system of claim 1 wherein said core comprises an aqueous solution having a diameter of from 0.0001 to 1 mm.

3. The encapsulation system of claim 1 wherein water comprises 10–90% average percentage by weight of the encapsulation system.

4. The encapsulation system of claim 3 wherein said hydrophobic particles comprise microcapsules.

5. The encapsulation system of claim 2 wherein microcapsules are admixed with the spherical encapsulated system.

6. The encapsulation system of claim 2 wherein non-encapsulated particles are admixed with the spherical encapsulated system.

7. The encapsulation system of claim 6 wherein there is at least one component present within the encapsulation system selected from the group consisting of pharmaceuticals, flavorings, vitamins, dyes, pigments, reactants, moisturizers, emollients, bleaching agents, whitening agents, lightening agents, darkening agents, radiation absorbing materials, reflective materials, catalysts/reactants, enzymes, pheromones, bioactive ingredients, inert materials, solutions of salts and oils.

8. The encapsulation system of claim 2 wherein said aqueous liquid comprises from 40–98% percent by weight of said encapsulation system and said hydrophobic particles comprise from 2 to 60% by weight of said encapsulation system.

9. An encapsulation system comprising droplet cores of aqueous liquids having diameters of from 0.0001 to 0.5 mm of aqueous liquid having a surface, said droplets having a stabilizing layer comprising hydrophobic particles with a volume weighted mean particle diameter of from 0.05 to 25 micrometer hydrophobic particles on said surface, said stabilizing layers being generally spherical, with at least 25% by number of all droplets encapsulated by hydrophobic particles in said encapsulated system having less than a 25% deviation in diameter in cross-sections.

10. The encapsulation system of claim 9 wherein said layer of hydrophobic particles comprises a layer of particles with less than 80% by number of said particles being bonded to any adjacent particle.

11. The encapsulation system of claim 9 wherein at least 30% by number of hydrophobic particles in said layer of hydrophobic particles are bonded to adjacent particles.

12. A method for providing a stable encapsulant system comprising providing a mass of hydrophobic particles having a volume weighted mean diameter of between 0.05 and 25 micrometers, providing droplets of an aqueous medium to the mass of particles, gently mixing the fine particles of aqueous medium and the hydrophobic particles to form a stable encapsulant system of droplets of said aqueous medium encapsulated by a shell of particles.

13. The method of claim 12 wherein mixing is done at a low energy mixing rate of from 0.00005 to 5.0 kg m$^2$ sec−1.

14. The method of claim 12 wherein mixing is done at a low energy mixing rate of from 0.0005 to 1.0 kg m$^2$ sec−1.

15. The method of claim 13 wherein said mixing is performed in the presence of at least one component present within the encapsulant system selected from the group consisting of pharmaceuticals, flavorings, vitamins, dyes, pigments, reactants, moisturizers, emollients, bleaching agents, whitening agents, lightening agents, darkening agents, radiation absorbing materials, reflective materials, catalysts/reactants, enzymes, pheromones, bioactive ingredients, inert materials, solutions of salts and oils.

16. The method of claim 12 wherein said droplets comprise an aqueous solution having an average droplet diameter of from 0.0001 mm to 1 mm.

17. The method of claim 16 wherein water comprises 10–75% average percentage by weight of the encapsulation system.

18. The method of claim 16 wherein said hydrophobic particles comprise microcapsules.

19. The method of claim 18 wherein said microcapsules comprise a continuous shell surrounding a liquid fill.

20. The method of claim 19 wherein said liquid fill comprises a hydrophobic liquid.

21. A method according to claim 12 wherein said mixing is effected by a rotated bed/water atomization process.

22. The encapsulation system of claim 2 wherein said hydrophobic particles comprise fumed silica having non-fumed reactive sites or non-fumed non-reactive sites that add to the hydrophobicity of a surface of the hydrophobic particles.

23. The method of claim 12 wherein microcapsules are present in admixture with the hydrophobic particles while the droplets of aqueous medium are added to the hydrophobic particles.

24. The method of claim 12 wherein microcapsules are added in admixture with the hydrophobic particles while the droplets of aqueous medium are being added to the hydrophobic particles.

25. The method of claim 12 wherein microcapsules are added to the hydrophobic particles after the droplets of aqueous medium have been added to the hydrophobic particles.

* * * * *